(12) United States Patent
Jan et al.

(10) Patent No.: US 6,500,998 B1
(45) Date of Patent: Dec. 31, 2002

(54) AROMATIC ALKYLATION PROCESS USING UZM-5 AND UZM-6 ALUMINOSILICATES

(75) Inventors: Deng-Yang Jan, Elk Grove Village, IL (US); Gregory J. Lewis, Mt. Prospect, IL (US); Jaime G. Moscoso, Mt. Prospect, IL (US); Mark A. Miller, Niles, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/062,691

(22) Filed: Jan. 31, 2002

Related U.S. Application Data

(62) Division of application No. 09/706,285, filed on Nov. 3, 2000, now Pat. No. 6,388,157.

(51) Int. Cl.$^7$ ................................................ C07C 4/24
(52) U.S. Cl. ...................................................... 585/475
(58) Field of Search ................................. 585/475, 470

(56) References Cited

U.S. PATENT DOCUMENTS 5,522,984 A  *  6/1996  Gajda et al. ................. 208/120

* cited by examiner

*Primary Examiner*—Thuan D. Dang
(74) *Attorney, Agent, or Firm*—John G. Tolomei; Frank S. Molinaro

(57) ABSTRACT

A process for transalkylating a polyalkylated aromatic compound with a non-alkylated aromatic compound using a new family of related crystalline aluminosilicate zeolites has been developed. These zeolites are represented by the empirical formula:

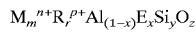

where M is an alkali or alkaline earth metal such as lithium and strontium, R is a nitrogen containing organic cation such as tetramethyl-ammonium and E is a framework element such as gallium.

7 Claims, No Drawings

AROMATIC ALKYLATION PROCESS USING UZM-5 AND UZM-6 ALUMINOSILICATES

CROSS-REFERENCE TO RELATED APPLICATION

This application is a divisional of copending U.S. application Ser. No. 09/706,285 filed on Nov. 3, 2000, now U.S. Pat. No. 6,388,157 the contents of which are incorporated by reference in their entirety.

FIELD OF THE INVENTION

This invention relates to an alkylation process using a family of related crystalline aluminosilicate zeolites, examples of which have been designated UZM-5, UZM-5P and UZM-6. These zeolites are structurally different from other zeolites.

BACKGROUND OF THE INVENTION

Zeolites are crystalline aluminosilicate compositions which are microporous and which have a three dimensional oxide framework formed from corner sharing $AlO_2$ and $SiO_2$ tetrahedra. Numerous zeolites, both naturally occurring and synthetically prepared are used in various industrial processes. One such process is the alkylation of aromatics with olefins and especially the alkylation of benzene with ethylene or propylene. The reaction between benzene and propylene produces mostly cumene. Cumene is an important industrial compound because it is a source of phenol, acetone, which are obtained by the oxidation of Cumene and subsequent acid-catalyzed decomposition of the intermediate hydroperoxide. Acid catalysts are used to catalyze this reaction with the most common catalysts being zeolites and particularly zeolite beta.

Applicants have synthesized a new family of crystalline aluminosilicate zeolites which have good activity for the alkylation of aromatics. These crystalline zeolitic compositions have a unique x-ray diffraction pattern and have an empirical formula on an anhydrous basis in terms of molar ratios of $$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of quaternary ammonium ions, protonated amines, protonated diamines, protonated alkanolamines, quaternary alkanolammonium ions and diquaternary ammonium ions, and mixtures thereof, "r" is the mole ratio of R to (Al+E) and has a value of about 0.25 to about 3.0, E is an element selected from the group consisting of Ga, Fe, Cr, In and B, "x" is the mole fraction of E and varies from 0 to about 0.5, "n" is the weighted average valence of M and has a value of +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m\cdot n+r\cdot p+3+4\cdot y)/2.$$

Specific members of this family of zeolites are UZM-5, UZM-5P and UZM-6.

SUMMARY OF THE INVENTION

This invention relates to a process for the alkylation of aromatic compounds using a new family of zeolites. Accordingly, one embodiment of the invention is a process for transalkylating an aromatic compound comprising reacting under transalkylation conditions a polyalkylated aromatic compound with a nonalkylated aromatic compound, wherein at least one alkyl group is transferred from the polyalkylated aromatic compound to the nonalkylated aromatic compound in the presence of a microporous crystalline zeolite having a composition in the as synthesized form on an anhydrous basis in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is an element selected from the group consisting of Ga, Fe, In and Cr and B, "x" is the mole fraction of E and varies from 0 to 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m\cdot n+r\cdot p+3+4y)/2$$

The zeolite characterized in that it has at least two x-ray diffraction peaks, one at a d-spacing of 3.9±0.12 Å and one at 8.6±0.2 Å.

In a particular embodiment, the zeolite catalyst has been designated UZM-5 and has the x-ray diffraction pattern having at least the d-spacings and intensities set forth in Table A:

TABLE A

| UZM-5 | | |
|---|---|---|
| 2-θ | d(Å) | I/I₀ % |
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.83–3.96 | w–s |
| 24.16–23.33 | 3.68–3.81 | vs |
| 30.48–29.55 | 2.93–3.02 | w–m |
| 31.94–30.92 | 2.80–2.89 | w–m |
| 44.83–43.47 | 2.02–2.08 | w |

One specific embodiment involves the alkylation of benzene with propylene to give cumene.

Another embodiment of the invention is a transalkylation process comprising reacting under transalkylation reaction conditions a polyalkylated aromatic compound with a nonalkylated aromatic compound in the presence of the zeolites described above, wherein at least one alkyl group is transferred from the polyalkylated aromatic compound to the nonalkylated aromatic compound.

These and other objects and embodiments will become more apparent after the following detailed description of the invention.

DETAILED DESCRIPTION OF THE INVENTION

An essential feature of applicants' process is a new family of zeolites. In its as-synthesized form this family of zeolites has a composition on an anhydrous basis that is represented by the formula:

$$M_m^{n+}R_r^{p+}Al_{(1-x)}E_xSi_yO_z$$

where M is an exchangeable cation and is selected from the group consisting of alkali and alkaline earth metals. Specific examples of the M cations include but are not limited to lithium, sodium, potassium, cesium, strontium, calcium, magnesium, barium and mixtures thereof. The value of "m" which is the mole ratio of M to (Al+E) varies from 0 to 1.2. R is a nitrogen containing organic cation and is selected from the group consisting of pronated amines, protonated diamines, protonated alkanolamines, quaternary ammonium ions, diquaternary ammonium ions, quaternized alkanolammonium ions and mixtures thereof. The value of "r" which is the mole ratio of R to (Al+E) varies from about 0.25 to about 3.0. The value of "n" which is the weighted average valence of M varies from +1 to about +2. The value of "p", which is the average weighted valence of the organic cation has a value from about +1 to about +2. E is an element which is present in the framework and is selected from the group consisting of gallium, iron, chromium, indium, boron and mixtures thereof. The value of "x" which is the mole fraction of E varies from 0 to about 0.5. The ratio of silicon to (Al+E) is represented by "y" which varies from about 5 to about 12, while the mole ratio of O to (Al+E) is represented by "z" and" has a value given by the equation:

$$z=(m \cdot n+r \cdot p+3+4 \cdot y)/2.$$

When M is only one metal, then the weighted average valence is the valence of that one metal, i.e. +1 or +2. However, when more than one M metal is present, the total amount of:

$$M_m^{n+}=M_{m1}^{(n1)+}+M_{m2}^{(n2)+}+M_{m3}^{(n3)+}+$$

and the weighted average valence "n" is given by the equation.

$$n = \frac{m_1 \cdot n_1 + m_2 \cdot n_2 + m_3 \cdot n_3 + \cdots}{m_1 + m_2 + m_3 \cdots}.$$

Similarly when only one R organic cation is present, the weighted average valence is the valence of the single R cation, i.e., +1 or +2. When more than one R cation is present, the total amount of R is given by the equation:

$$R_r^{p+}=R_{r1}^{(p1)+}+R_{r2}^{(p2)+}+R_{r3}^{(p3)+}$$

and the weighted average valence "p" is given by the equation:

$$p = \frac{p_1 \cdot r_1 + p_2 \cdot r_2 + p_3 \cdot r_3 + \cdots}{r_1 + r_2 + r_3 + \cdots}.$$

The zeolitic compositions are prepared by a hydrothermal crystallization of a reaction mixture prepared by combining reactive sources of R, aluminum, silicon and optionally E and/or M in aqueous media. Accordingly, the aluminum sources include, but are not limited to, aluminum alkoxides, precipitated alumina, aluminum hydroxide, aluminum salt and aluminum metal. Specific examples of aluminum alkoxides include, but are not limited to aluminum ortho sec-butoxide, and aluminum orthoisopropoxide. Sources of silica include but are not limited to tetraethylorthosilicate, fumed silicas, precipitated silicas and colloidal silica. Sources of the M metals include the halide salts, nitrate salts, acetate salts, and hydroxides of the respective alkali or alkaline earth metals. Sources of the E elements include but are not limited to alkali borates, boric acid, precipitated gallium oxyhydroxide, gallium sulfate, ferric sulfate, ferric chloride, chromium chloride, chromium nitrate, indium chloride and indium nitrate. When R is a quaternary ammonium cation, the sources include the hydroxide, and halide compounds. Specific examples include without limitation tetramethylammonium hydroxide, tetraethylammonium hydroxide, hexamethonium bromide, tetramethylammonium chloride, methyltriethylammonium hydroxide. R may also be neutral amines, diamines, and alkanolamines. Specific examples are triethanolamine, triethylamine, and N,N,N',N' tetramethyl-1,6-hexanediamine.

The reaction mixture containing reactive sources of the desired components can be described in terms of molar ratios of the oxides by the formula:

$$aM_{2/n}O:bR_{2/p}O:(1-c)Al_2O_3:cE_2O_3:dSiO_2:eH_2O$$

Where "a" is the mole ratio of the oxide of M and has a value of 0 to about 2, "b" is the mole ratio of the oxide of R and has a value of about 1.5 to about 30, "d" is the mole ratio of silica and has a value of about 5 to about 30, "c" is the mole ratio of the oxide of E and has a value of 0 to about 0.5, and "e" is the mole ratio of water and has a value of about 30 to about 6000. The reaction mixture is now reacted at reaction conditions including a temperature of about 100° C. to about 175° C. and preferably from about 140° C. to about 160° C. for a period of about 12 hours to about 14 days and preferably for a time of about 2 days to about 5 days in a sealed reaction vessel under autogenous pressure. After crystallization is complete, the solid product is isolated from the heterogeneous mixture by means such as filtration or centrifugation, and then washed with de-ionized water and dried in air at ambient temperature up to about 100° C.

As synthesized, the zeolites will contain some of the exchangeable or charge balancing cations in its pores. These exchangeable cations can be exchanged for other cations, or in the case of organic cations, they can be removed by heating under controlled conditions. All of these methods are well known in the art.

The crystalline zeolites are characterized by a three-dimensional framework structure of at least $SiO_2$ and $AlO_2$ tetrahedral units. These zeolites are further characterized by their unique x-ray diffraction pattern. The x-ray diffraction pattern has at least two peaks: one peak at a d-spacing of about 3.9±0.12 Å and one peak at a d-spacing of about 8.6±0.20 Å. To allow for ready reference, the different structure types and compositions of crystalline zeolites have been given arbitrary designation of UZM-h, where "h" is an integer starting at one and where for example "1" represents a framework of structure type "1". That is one or more zeolitic composition with different empirical formulas can have the same structure type "h", e.g. "1".

In this respect, the following species can be identified by their x-ray diffraction patterns which have at least the d-spacing and relative intensities set forth in Tables A to C.

TABLE A

UZM-5

| 2-θ | d(Å) | I/I₀ % |
|---|---|---|
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.83–3.96 | w–s |
| 24.16–23.33 | 3.68–3.81 | vs |
| 30.48–29.55 | 2.93–3.02 | w–m |
| 31.94–30.92 | 2.80–2.89 | w–m |
| 44.83–43.47 | 2.02–2.08 | w |

TABLE B

UZM-5P

| 2-θ | d(Å) | I/I₀ % |
|---|---|---|
| 6.31–5.19 | 14.00–17.00 | w–vs |
| 7.96–7.56 | 11.10–11.70 | w–m |
| 10.52–10.04 | 8.40–8.80 | m–s |
| 16.56–15.67 | 5.35–5.65 | w–m |
| 19.49–18.87 | 4.55–4.70 | w–m |
| 23.52–22.09 | 3.78–4.02 | w–vs |
| 24.03–23.39 | 3.70–3.80 | w–vs |
| 30.81–29.76 | 2.90–3.00 | w–m |
| 31.94–30.81 | 2.80–2.90 | w–m |
| 45.30–43.04 | 2.00–2.10 | w–m |

TABLE C

UZM-6

| 2-θ | d(Å) | I/I₀ % |
|---|---|---|
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.92–4.00 | m–vs |
| 24.16–23.33 | 3.83–3.96 | w–s |
| 30.48–29.55 | 3.68–3.81 | s–vs |
| 31.94–30.92 | 2.80–2.89 | m |
| 44.83–43.47 | 2.02–2.08 | w |

The zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m²/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50–200° C. and subjected to a calcination procedure at a temperature of about 450–700° C. for a period of about 1 to about 20 hours. This treatment effects conversion of the hydrogel to the corresponding alumina matrix.

The alkylation and preferably the monoalkylation of aromatic compounds involves reacting an aromatic compound with an olefin using the above described zeoltic catalyst. The olefins which can be used in the instant process are any of those which contain from 2 up to about 20 carbon atoms. These olefins may be branched or linear olefins and either terminal or internal olefins. Preferred olefins are ethylene, propylene and those olefins which are known as detergent range olefins. Detergent range olefins are linear olefins containing from 6 up through about 20 carbon atoms which have either internal or terminal double bonds. Linear olefins containing from 8 to 16 carbon atoms are preferred and those containing from 10 up to about 14 carbon atoms are especially preferred.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also can be substituted on the alkyl chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, etc.

The particular conditions under which the monoalkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. As a practical matter the pressure normally is in the range between about 200 and about 1,000 psig (1379–6985 kPa) but usually is in a range between about 300–600 psig (2069–4137 kPa). The alkylation of the alkylatable aromatic compounds with the olefins in the C2–C20 range can be carried out at a temperature of about 60° C. to about 400° C., and preferably from about 90° C. to about 250° C., for a time sufficient to form the desired product. In a continuous process this time can vary considerably, but is usually from about 0.1 to about 3 $hr^{-1}$ weight hourly space velocity with respect to the olefin. In particular, the alkylation of benzene with ethylene can be carried out at temperatures of about 200° C. to about 250° C. and the alkylation of benzene by propylene at a temperature of about 90° C. to about 200° C. The ratio of alkylatable aromatic compound to olefin used in the instant process will depend upon the degree of selective monoalkylation desired as well as the relative costs of the aromatic and olefinic components of the reaction mixture. For alkylation of benzene by propylene, benzene-to-olefin ratios may be as low as about 1 and as high as about 10, with a ratio of 2.5–8 being preferred. Where benzene is alkylated with ethylene a benzene-to-olefin ratio between about 1:1 and 8:1 is preferred. For detergent range olefins of C6–C20, a benzene-to-olefin ratio of between 5:1 up to as high as 30:1 is generally sufficient to ensure the desired monoalkylation selectivity, with a range between about 8:1 and about 20:1 even more preferred.

The zeolites of this invention can also be used to catalyze transalkylation. By "transalkylation" is meant that process where an alkyl group on one aromatic nucleus is intermolecularly transferred to a second aromatic nucleus. A preferred transalkylation process is one where one or more alkyl groups of a polyalkylated aromatic compound is transferred to a nonalkylated aromatic compound, and is exemplified by reaction of diisopropylbenzene with benzene to give two molecules of cumene. Thus, transalkylation often is utilized to add to the selectivity of a desired selective monoalkylation by reacting the polyalkylates invariably formed during alkylation with nonalkylated aromatic to form additional monoalkylated products. For the purposes of this process, the polyalkylated aromatic compounds are those formed in the alkylation of alkylatable aromatic compounds with olefins as described above, and the nonalkylated aromatic compounds are benzene, naphthalene, anthracene, and phenanthrene. The reaction conditions for transalkylation are similar to those for alkylation, with temperatures being in the range of about 100 to about 250° C., pressures in the range of 100 to about 750 psig, and the molar ratio of unalkylated aromatic to polyalkylated aromatic in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene etc.

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate reaction mixture was prepared in the following manner. Aluminum sec-butoxide (95+%), 58.75 g, was added to 836.34 g TEAOH (35%) with vigorous stirring. To this mixture, 294.73 g colloidal silica, (Ludox AS-40, 40% $SiO_2$) was added, followed by the addition of 10.18 g distilled water. The reaction mixture was homogenized for 1 hr with a high-speed mechanical stirrer, and then aged in teflon bottles overnight at 95° C. After the aging step, the reaction mixture was recombined and analyzed; the analysis indicated a silicon content of 4.67%.

A 500 g portion of this reaction mixture was treated with TMACl solution consisting of 11.77 g TMACl (97%) dissolved in 23.0 g distilled water while applying vigorous mixing. After a half hour of homogenization the reaction mixture was distributed among 8 teflon-lined autoclaves. The autoclaves were all placed in ovens set at 150° C., where the reaction mixtures were digested for 4 days at autogenous pressures. The solid products were recovered by centrifugation, washed, and dried at 95° C.

The composition of the isolated product consisted of the mole ratios Si/Al=6.88, N/Al=0.83 and C/N=6.05. Scanning Electron Microscopy (SEM) showed the crystallites to consist of clustered platelets approximately 100–300 nm across. Characterization by powder X-ray diffraction (XRD) showed the lines in the pattern to be those for the new material designated UZM-5. Table 1 below shows lines characteristic of the phase. A portion of the sample was calcined, by ramping to 540° C. at 2° C./min in $N_2$, holding at 540° C. in $N_2$ for 1 hr followed by 7 hr dwell in air, also at 540° C. The BET surface area was found to be 530 $m^2/g$, and the micropore volume was 0.22 cc/g.

TABLE 1

| 2-θ | d(Å) | $I/I_o$ % |
|---|---|---|
| 6.24 | 14.15 | m |
| 7.90 | 11.18 | m |
| 10.32 | 8.57 | w–m |
| 12.00 | 7.37 | m |
| 15.80 | 5.60 | m–s |
| 16.34 | 5.42 | m |
| 19.05 | 4.66 | w–m |
| 22.00 | 4.04 | m |
| 22.86 | 3.89 | m |
| 23.80 | 3.74 | vs |
| 27.40 | 3.25 | w |
| 30.14 | 2.96 | w |
| 30.90 | 2.89 | w |
| 31.60 | 2.83 | m |
| 33.20 | 2.70 | w |
| 34.56 | 2.59 | w |
| 36.64 | 2.45 | w |
| 44.32 | 2.04 | w |

EXAMPLE 2

An aluminosilicate reaction mixture was prepared in the following manner: Al(Osec-Bu)$_3$ (95+%), 116.09 g, was added to 1983.17 g TEAOH (35%) and 1.86 g de-ionized water with vigorous stirring. Then 698.88 g Ludox AS-40 was added, with continued stirring. After an hour of homogenization, the aluminosilicate reaction mixture was placed in several teflon bottle and aged at 95° C. for 3 days. After the aging process, elemental analysis showed the mixture contained 5.01% Si and had a Si/Al ratio of 10.03. This reaction mixture was designated Mixture A. A portion of this aluminosilicate reaction mixture, 40.0 g, was placed in a beaker where it was stirred vigorously. Separately, 0.78 g TMACl (97%) was dissolved in 15.0 g de-ionized water. This solution was added to the stirring aluminosilicate reaction mixture in a dropwise fashion. The mixture was allowed to homogenize further for about an hour. The reaction mixture was then placed in a teflon-lined autoclave and digested at 150° C. for 6 days at autogenous pressures. The solid product was isolated by centrifugation, washed with de-ionized water, and dried at 95° C.

The product had an x-ray pattern designated to be UZM-6. Scanning Electron Microscopy (SEM) showed the material to consist of plate-like crystals about 0.1–0.4µ across and less than 0.05µ thick. The Si/Al ratio of the product UZM-6 was 8.34 by elemental analysis. The BET surface area of the sample was 520 m$^2$/g, with a micropore volume of 0.21 cc/g. Characteristic lines in the x-ray diffraction pattern are given in Table 2.

TABLE 2

| 2-θ | d(Å) | I/I$_o$ % |
|---|---|---|
| 6.14 | 14.38 | m |
| 7.76 | 11.38 | m |
| 10.12 | 8.73 | m |
| 11.82 | 7.48 | m |
| 15.68 | 5.65 | s |
| 16.30 | 5.43 | m |
| 18.98 | 4.67 | m |
| 20.32 | 4.37 | w |
| 21.86 | 4.06 | m |
| 22.42 | 3.96 | s |
| 22.78 | 3.90 | m |
| 23.68 | 3.75 | vs |
| 25.24 | 3.53 | w |
| 26.28 | 3.39 | w |
| 26.88 | 3.31 | m |
| 27.34 | 3.26 | m |
| 29.64 | 3.01 | m |
| 30.08 | 2.97 | w |
| 31.44 | 2.84 | w |
| 33.20 | 2.70 | w |
| 44.14 | 2.05 | w |

EXAMPLE 3

An aluminosilicate reaction mixture was prepared in an identical manner to Mixture A described in example 2. However, the reaction mixture was determined to be slightly different by analysis with a Si content of 4.79 wt % and a Si/Al ratio of 9.59. A portion of this aluminosilicate reaction mixture, 1100 g, was placed in a large beaker equipped with a high-speed stirrer. Separately, a solution was prepared by dissolving 4.14 g LiCl and 21.43 g TMACl (97%) in 65 g de-ionized water. This solution was added dropwise to the aluminosilicate reaction mixture with stirring and was homogenized for an hour. The reaction mixture was then transferred to a static 2-L Parr reactor and digested at 150° C. for 3 days at autogenous pressure. The solid product was isolated by filtration, washed with de-ionized water and dried at 95° C.

Powder x-ray diffraction on a sample of the product showed the pattern to be consistent with that for UZM-6. The Si/Al ratio was 7.58. The BET surface area was 512 m$^2$/g, while the micropore volume was found to be 0.18 cc/g. SEM of the calcined product showed it to consist of bent plate crystals, sometimes stacked, up to 0.1–0.4µ across and less that 0.05µ thick. Characteristic lines in the x-ray diffraction pattern are given in Table 3.

TABLE 3

| 2-θ | d(Å) | I/I$_o$ % |
|---|---|---|
| 6.28 | 14.07 | m |
| 7.84 | 11.27 | s |
| 10.22 | 8.65 | m |
| 11.92 | 7.42 | m |
| 15.93 | 5.56 | m |
| 18.98 | 4.67 | m |
| 21.98 | 4.04 | w |
| 22.52 | 3.95 | vs |
| 22.92 | 3.88 | m |
| 23.76 | 3.74 | vs |
| 26.33 | 3.38 | w |
| 26.92 | 3.31 | m |
| 31.36 | 2.85 | m |
| 33.26 | 2.69 | m |
| 44.24 | 2.05 | w |

EXAMPLE 4

Samples from examples 1 to 3 were tested for alkylation activity by using an ethylbenzene disproportionation test. The materials were converted to the proton form before testing. The UZM-6 from example 3 was calcined in air at 350° C. for 1.5 hours, 450° C. for 1.5 hours and 7 hours at 580° C. and ion exchanged with ammonium chloride, three times at 80° C. for 2 hours The UZM-6 from example 2 was calcined at 520° C. for 1 hour in N$_2$, followed by 19 hours in air. The UZM-5 from example 1 was calcined at 520° C. for 10 hr. The calcined samples were sized to 40–60 mesh and loaded (250 mg) into a quartz tube (11 mm i.d.) reactor residing in a furnace. The outlet pressure at the reactor inlet was atmospheric pressure. The samples were pretreated at 250° C. in a flow of N$_2$. The temperature was brought down to 150° C. and then the feed was introduced. The feed consisted of the N$_2$ flow passing through an ethylbenzene saturator held at 0° C., with the N$_2$ flow controlled at 150 cc/min. While the flow remained constant, the sample was exposed to the feed and reaction products were examined at 150° C., 150° C., 125° C., 175° C., 200° C., 230° C., and 175° C. The product effluents are analyzed by an on-line GC to measure activity and selectivity. Results from the second 150° C. and the 230° C. product collections are given in Table 4.

TABLE 4

| | UZM-5, Ex. 1 | | UZM-6, Ex. 2 | | UZM-6, Ex. 3 | |
|---|---|---|---|---|---|---|
| Temperature (deg C.) | 150 | 230 | 150 | 230 | 150 | 230 |
| Flow Rate (cc/min) | 150 | 150 | 150 | 150 | 150 | 150 |
| Methane/Ethane | 0.02 | 0 | 0.03 | 0.06 | 0 | 0.08 |
| C4's | 0 | 0 | 0.02 | 0.07 | 0.1 | 0.11 |
| Benzene | 0.09 | 0.18 | 0.39 | 1.21 | 0.64 | 2.63 |
| Ethylcyclohexane | 0 | 0 | 0 | 0 | 0 | 0 |
| Toluene | 0 | 0 | 0.04 | 0.04 | 0.04 | 0.05 |
| Ethylbenzene | 99.72 | 99.46 | 98.69 | 96.02 | 97.86 | 91.97 |
| p-Xylene | 0 | 0 | 0 | 0 | 0 | 0 |
| m-Xylene | 0 | 0 | 0 | 0 | 0 | 0 |
| o-Xylene | 0 | 0 | 0 | 0 | 0 | 0 |
| 1E4MBZ | 0 | 0 | 0 | 0 | 0 | 0 |
| 1E3MBZ | 0 | 0 | 0 | 0 | 0 | 0 |
| 1E2MBZ | 0 | 0 | 0 | 0 | 0 | 0 |
| 13DEBZ | 0.09 | 0.22 | 0.41 | 1.63 | 0.76 | 3.24 |

TABLE 4-continued

|  | UZM-5, Ex. 1 | | UZM-6, Ex. 2 | | UZM-6, Ex. 3 | |
| --- | --- | --- | --- | --- | --- | --- |
| 14DEBZ | 0.08 | 0.13 | 0.4 | 0.82 | 0.55 | 1.6 |
| 12DEBZ | 0 | 0 | 0.03 | 0.15 | 0.05 | 0.28 |
| 14DIPBZ | 0 | 0 | 0 | 0 | 0 | 0.02 |
| 135TEBZ | 0 | 0 | 0 | 0 | 0 | 0 |
| 124TEBZ | 0 | 0 | 0 | 0 | 0 | 0 |
| EB CONV | 0.28 | 0.54 | 1.31 | 3.98 | 2.14 | 8.03 |

EXAMPLE 5

This example demonstrates the capability of UZM-6 to catalyze the synthesis of ethylbenzene from benzene and ethylene. The zeolite from example 3 was converted to the proton by the same procedure as in example 4. The zeolite was then bound with Plural SB alumina in a 70% zeolite/30% alumina formulation and formed into 1/16" diameter extrudates. The extrudates were then calcined at 550° C. for 2 hr. The test employs a 7/8" diameter stainless steel reactor which is loaded with 40 cc of the catalyst. The benzene and ethylene are mixed on-line to a 3/1 benzene/ethylene ratio and then pre-heated before entering the reactor. The olefin was added at a rate of 0.45 hr$^{-1}$ LHSV. The testing was done with an effluent recycle to control the free olefin at the reactor inlet. The reaction was carried out at 500 psig. Activity and selectivity data were collected at 200° C. and 230° C. The selectivities to alkylated products are shown in Table 5.

TABLE 5

Ethylbenzene Synthesis with UZM-6

| Hours on Stream | 60 | 271 |
| --- | --- | --- |
| Inlet temperature | 200° C. | 230° C. |
| Ethylbenzene | 80.31 | 74.95 |
| Diethylbenzenes | 16.26 | 19.95 |
| Triethylbenzenes | 2.46 | 3.92 |
| Tetraethylbenzenes | 0.22 | 0.37 |
| Alkylated products | 99.25 | 99.19 |

We claim as our invention:

1. A transalkylation process comprising reacting under transalkylation reaction conditions a polyalkylated aromatic compound with a nonalkylated aromatic compound, wherein at least one alkyl group is transferred from the polyalkylated aromatic compound to the nonalkylated aromatic compound in the presence of a microporous crystalline zeolite having a composition in the as synthesized form on an anhydrous basis in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is an element selected from the group consisting of Ga, Fe, In and Cr and B, "x" is the mole fraction of E and varies from 0 to 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m \cdot n + r \cdot p + 3 + 4 \cdot y)/2$$

the zeolite characterized in that it has at least two x-ray diffraction peaks, one at a d-spacing of 3.9±0.12 Å and one at 8.6±0.2 Å.

2. The process of claim 1 where the zeolite has a x-ray powder diffraction pattern which contains at least the d-spacings and relative intensities of one of Tables A to C.

3. The process of claim 1 where the alkyl groups of the polyalkylated aromatic compound contain from about 2 up to about 20 carbon atoms.

4. The process of claim 3 where the alkyl groups contain from 6 up to about 20 carbon atoms.

5. The process of claim 4 where the alkyl groups contain from 8 up to about 16 carbon atoms.

6. The process of claim 1 where the nonalkylated aromatic compound is selected from the group consisting of benzene, naphthalene, anthracene, phenanthrene, and substituted derivatives thereof.

7. The process of claim 1 where said polyalkylated aromatic compound is a polyisopropyl benzene and the nonalkylated aromatic compound is benzene.

* * * * *